(12) United States Patent
Ruppert et al.

(10) Patent No.: US 9,295,534 B2
(45) Date of Patent: Mar. 29, 2016

(54) PRODUCTION OF INDIVIDUAL DENTAL PROSTHESES VIA CAD/CAM AND RAPID MANUFACTURING/RAPID PROTOTYPING FROM DATA OF THE DIGITAL IMPRESSION

(75) Inventors: Klaus Ruppert, Maintal (DE); Mario Beyer, Bad Homburg (DE)

(73) Assignee: Heraeus Kulzer GmbH, Hanau (DE)

( * ) Notice: Subject to any disclaimer, the term of this patent is extended or adjusted under 35 U.S.C. 154(b) by 482 days.

(21) Appl. No.: 13/513,809

(22) PCT Filed: Nov. 5, 2010

(86) PCT No.: PCT/EP2010/006753
§ 371 (c)(1),
(2), (4) Date: Jun. 4, 2012

(87) PCT Pub. No.: WO2011/066895
PCT Pub. Date: Jun. 9, 2011

(65) Prior Publication Data
US 2012/0258430 A1    Oct. 11, 2012

(30) Foreign Application Priority Data

Dec. 4, 2009  (DE) .................. 10 2009 056 752

(51) Int. Cl.
*G06F 19/00*    (2011.01)
*B29C 39/00*    (2006.01)
*A61C 3/00*    (2006.01)
*A61C 11/00*    (2006.01)
(Continued)

(52) U.S. Cl.
CPC ............. *A61C 13/0004* (2013.01); *A61C 13/10* (2013.01); *A61C 9/0053* (2013.01)

(58) Field of Classification Search
CPC .... A61C 11/00; A61C 13/0004; A61C 13/01; A61C 13/10; A61C 13/38; A61C 9/004; A61C 9/0053; A61C 19/04; A61C 7/00; A61C 13/0003; A61C 9/00; A61C 19/003; G06Q 50/22; G06F 17/50; A61K 6/09; A61K 6/083; C08L 75/16; C08L 33/00
USPC ............. 700/98, 97, 199; 705/2; 433/24, 215; 264/18, 16, 17, 221, 222, 494; 523/115, 116, 117; 524/456, 493, 494
See application file for complete search history.

(56) References Cited

U.S. PATENT DOCUMENTS 6,322,728 B1    11/2001    Brodkin et al.
6,881,360 B2    4/2005    Stange et al.
(Continued)

FOREIGN PATENT DOCUMENTS

DE    2619213 C2    10/1982
DE    4025728 A1    2/1992
(Continued)

*Primary Examiner* — Mohammad Ali
*Assistant Examiner* — Md Azad
(74) *Attorney, Agent, or Firm* — Norris McLaughlin & Marcus, P.A.; Christa Hildebrand

(57) ABSTRACT

A method for automated manufacture of dentures including providing a digital data set of the individual denture to be produced, a digital separation of the model into dental arch and gingival, producing the dental arch from a ceramic or plastic material using cutting technology, producing the denture base through generative or ablative procedures from predominantly (meth-)acrylate-based plastic materials, connecting the dental arch and gingiva through bonding or joining or a combination of bonding and joining.

11 Claims, 2 Drawing Sheets

(51) Int. Cl.
*A61C 9/00* (2006.01)
*A61C 13/08* (2006.01)
*A61C 13/00* (2006.01)
*A61C 13/10* (2006.01)
*A61C 13/20* (2006.01)

(56) References Cited

U.S. PATENT DOCUMENTS

| | | | |
|---|---|---|---|
| 8,386,061 B2* | 2/2013 | Violante et al. | 700/98 |
| 2009/0087818 A1* | 4/2009 | O'Brien et al. | 433/223 |
| 2009/0248184 A1* | 10/2009 | Steingart et al. | 700/98 |
| 2009/0287332 A1 | 11/2009 | Adusumilli et al. | |
| 2010/0332253 A1* | 12/2010 | Adusimilli et al. | 705/2 |

FOREIGN PATENT DOCUMENTS

| | | |
|---|---|---|
| DE | 10114290 A1 | 10/2002 |
| DE | 10150256 A1 | 7/2003 |
| DE | 202006006286 U1 | 8/2007 |
| DE | 102006010665 A1 | 9/2007 |
| DE | 10 2007 002178 A1 | 7/2008 |
| DE | 102007013065 A1 | 9/2008 |
| EP | 1243340 A2 | 9/2002 |
| EP | 1 704 831 A1 | 9/2006 |
| EP | 1 864 627 A2 | 12/2007 |
| WO | WO2004086999 A1 | 10/2004 |
| WO | WO 2006050452 A2 * | 5/2006 |
| WO | WO2008081003 A1 | 7/2008 |
| WO | WO 2011066895 A1 | 6/2011 |

* cited by examiner

PRODUCTION OF INDIVIDUAL DENTAL PROSTHESES VIA CAD/CAM AND RAPID MANUFACTURING/RAPID PROTOTYPING FROM DATA OF THE DIGITAL IMPRESSION

This is an application filed under 35 USC §371 of PCT/EP2010/006753, claiming priority to DE 102009 056 752.6 filed on Dec. 4, 2009.

BACKGROUND OF THE INVENTION

Full or partial dentures are manufactured according to basically known methods. These include, e.g., the conventional methods involving powder/liquid technology that have been known for a long time and are described in the literature (e.g. EP 1 243 230 A2, U.S. Pat. No. 6,881,360 B2 and "Dental Materials" in: Ullmann's Encyclopedia of Industrial Chemistry, Copyright 2002 by Wiley-VCH Verlag).

In general, three different main classes of materials for the manufacture of full dentures are known. These are polymethylmethacrylate (PMMA)-based two component materials [commercially available as Palapress, Paladur (Heraeus Kulzer, DE), SR 3/60® Quick (Ivoclar, LI), Degupress® (Degussa-Hüls, DE)]; PMMA-free hot-curing materials [commercially available, e.g., as Paladon® 65 (Heraeus Kulzer, DE), SR 3/60®, SR Ivocap® (Ivoclar, LI), Lucitone® (Dentsply, US)] and injection moulded masses for thermoplastic processing.

Thermoplastic materials are heated and injected into a hollow space, usually through an injection moulding method. A known method called "Polyapress®" is distributed, amongst others, by Bredent, Senden (DE). There have been numerous attempts to use polymers such as PVC, polyurethane, polyamide or polycarbonate (Ullmann's loc. cit. 5.1.5. Other Denture Resins.)

Moreover, there are methods that are based on light- or microwave-cured 1-component materials (e.g. Versyo.com® made by Heraeus Kulzer); (Ullmann's loc. cit. 5.1.3. Light-Cured Polymers, 5.1.4. Microwave-Cured Polymers).

The work steps required for preparation of the processing of the plastic materials are the same for all of these materials.

Moreover, techniques for the build-up of layers are known in dental engineering. These are used in combination with light-curing materials in most cases, for example for veneering metal crowns or production of a denture. The advantages of said methods include the level of control over the procedure and the ability to vary the colours in order to attain aesthetically pleasing dental work.

The use of Rapid Prototyping[1] methods in dental engineering has also been proposed. These involve working with layers that can be polymerised (DE 101 14 290 A1, DE 101 50 256 A1) or with ink jet powder printing (U.S. Pat. No. 6,322, 728 B1).

[1] Rapid Prototyping (German: schneller Prototypenbau) is a method for rapid production of sample components based on design data. Accordingly, rapid prototyping methods are manufacturing methods aiming to implement existing CAD data directly and rapidly in work pieces, if possible without manual detours or moulds. The relevant data interface for this group of methods is the STL format. The methods that have become known by the name of Rapid Prototyping since the 1980s are usually primary forming methods that build-up the work piece in layers from shapeless or neutral-shape material utilising physical and/or chemical effects.

Essentially, the production of full dentures involves the following steps, as illustrated in FIG. 2:
 dentist taking a silicone impression;
 fabrication of a dental plaster model by the dental technician to reflect the shape of the jaw;
 setting-up the artificial teeth in wax and carving the gingiva;
 trying-in and correcting, if applicable, done by the dentist or the dental laboratory;
 investing the corrected wax denture in dental plaster, silicone or agar-agar;
 removing the wax by boiling it out with hot water;
 inserting the artificial teeth in the mould thus produced;
 filling the hollow space thus generated with a denture plastic material (e.g. PalaXpress®);
 polymerising, finishing, and polishing the final denture.

Attempts are being made to an increasing degree to simplify this complex procedure. Accordingly, Heraeus Kulzer presented the Filou 28 product (EP 1 704 831 A1) at the IDS 2005. This was the first attempt to reduce the time needed for setting-up the artificial teeth in wax.

BRIEF SUMMARY OF THE INVENTION

Continued developments in the field of cutting technology (CAD/CAM) and generative fabrication technology of rapid prototyping as well as rapid manufacturing[2]) are being introduecd into prosthetics. This has been called "digitisation of dental technology". The disadvantage of said methods (e.g. stereolithography or selective laser melting) are the thus far unsatisfactory aesthetic features of the materials employed therein, since the technology thus far allows only single, and thus single-coloured, starting materials to be used. However, especially the manufacture of artificial teeth requires the use of multi-coloured single components for the end-product to imitate a natural appearance.

[2] The term, Rapid Manufacturing or (German: Schnelle Fertigung), refers to methods and production procedures for rapid and flexible production of components and series' through tool-less fabrication based directly on the CAD data. The materials that are used include glass, metal, ceramics, plastics, and novel materials (such as UV-hardening sol-gel, see e.g. Multi Jet Modeling) [...] Since Rapid Manufacturing always focuses on producing the end-product directly, it is fundamentally different from Rapid Prototyping and Rapid Tooling (German: Schneller Werkzeugbau).

It is already feasible using CAD/CAM cutting technology to process multi-coloured, layered plastic (e.g. Vita CAD-temp multicolor) or even ceramic materials (e.g. Vitablocs Triluxe) that make the finished tooth, the finished prosthetic work, appear very natural.

The technological developments of recent years mentioned above also include progress in digitalised impression-taking, such as, e.g., scan technologies (Lava C.O.S. made by 3M Espe, Bluecam made by Sirona, Hint ELC directScan) or virtual articulators and/or virtual set-up of the teeth.

The object is to further simplify the conventional production process that is described above. Moreover, the manufacture of aesthetically sophisticated dentures with layers of colours or colour hues is to be made feasible.

The object is met by the features of claim 1. Preferred embodiments are evident from the further claims. Preferably, the following steps are carried out at a suitable time in the procedure described above:

1. Providing data from digital impression-taking or digitisation of a common silicone functional impression.

2. producing a colour-layered plastic or ceramic dental arch through CAD/CAM. Owing to the colour layering, the dental arch meets sophisticated aesthetic requirements.

3. Preparation and fabrication of an imitation of the gingiva.

This procedure simplifies the current fabrication process significantly and thus helps to save time and costs. Expediently, the two main components, dental arch and gingiva, are firmly connected to each other after being produced by means of established bonding methods (Signum Zirconia Bond®, Signum Ceramic Bond® or Palabond® and Light-Curing Versyo® or Palabond® and an autopolymerising prosthetic plastic material (Paladur®, PalaXpress®) of the same gingival colour).

DETAILED DESCRIPTION OF THE INVENTION

Figure 1:
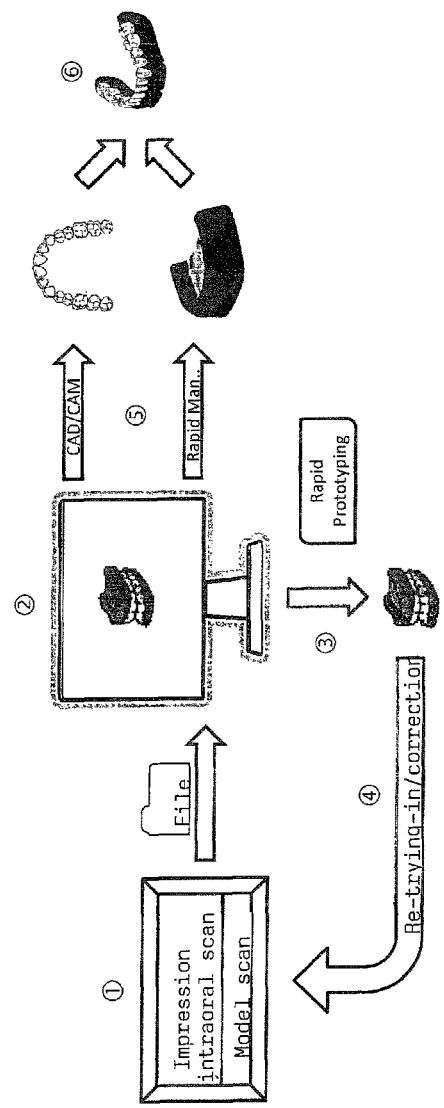
FIG. 1 shows a flow diagram of an exemplary embodiment of the manufacturing method according to the invention.
Figure 2:
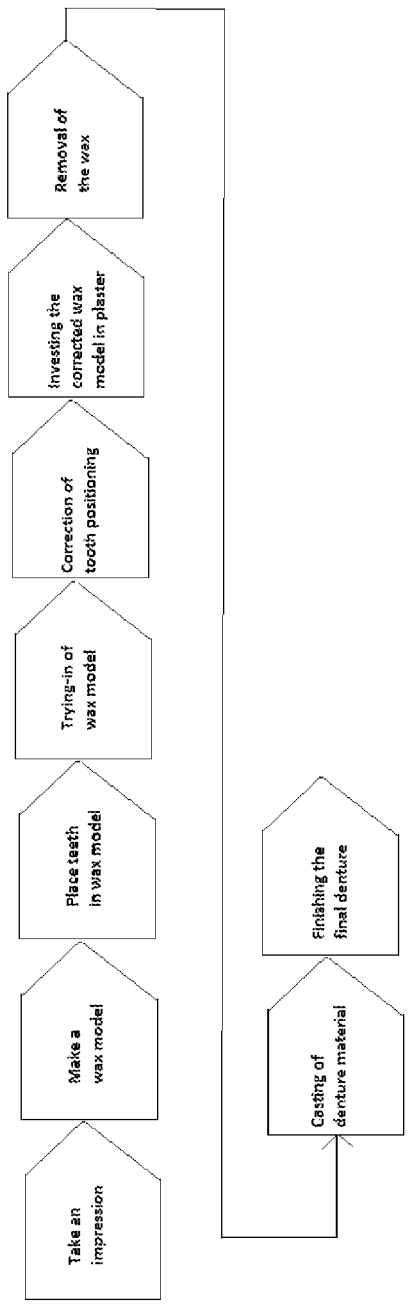
FIG. 2 shows another flow diagram showing the method according to the prior art.

In detail, the steps of the embodiment of the method according to the invention shown in FIG. 1 are as follows:
- conventional impression-taking by the dentist using silicone or intraoral scanner (1);
- submission of the digital model to the laboratory and digital set-up of the teeth (2);
- optional: Fabrication of a wax model by means of RP using, e.g. stereolithography with a dental wax that is approved as a medical product (3);
- optional: re-trying-in of said wax model in the patient and, if applicable, correction (4);
- optional: re-digitisation through a 3D scan;
- digital separation of the model into dental arch and gingival mass using respective recesses for the dental arch, and separate fabrication (5) thereof;
- union of the two main components through known dental bonding or joining methods;
- optional: reprocessing, such as, e.g., grinding-in and polishing;
- delivery to the customer.

The invention claimed is:

1. A method for automated manufacture of an individual denture comprising the steps of:
   providing a digital data set of a digital model of the individual denture to be produced;
   wherein the digital data set of the denture to be produced is provided through a virtual set-up of teeth by virtual articulation;
   digitally separating the digital model into separate dental arch digital data and gingiva mass digital data;
   producing based on the dental arch digital data a dental arch from a ceramic or plastic material using cutting technology;
   producing based on the gingiva mass digital data a gingiva mass using generative or ablative production from predominantly (meth-) acrylate-based plastic materials;
   connecting the dental arch and the gingiva mass through bonding or joining or a combination of bonding and joining to form the individual denture;
   wherein the production of the gingiva mass through generative rapid manufacturing methods is based on one of liquid or low- to high-viscosity, mono- or multi-functional (meth-)acrylates, methacrylates having a short-, medium- or long-chain aliphatic poly(ethylene glycol)- or dendrimer-based matrix and on mixtures of said individual components.

2. The method according to claim 1, wherein the digital model is separated into the dental arch digital data and the gingiva mass digital data using software.

3. The method according to claim 1, wherein the gingiva mass is produced through cutting technology.

4. The method according to claim 1, wherein the gingiva mass is produced through stereolithography.

5. The method according to claim 1, wherein the gingiva mass is produced through 3D ink jet printing.

6. The method according to claim 1,
   wherein the dental arch is produced through an ablative production carried out with tooth-coloured, multi-layered plastic material or tooth-coloured, multi-layered ceramic material.

7. The method according to claim 1, wherein the bonding of the dental arch and the gingiva mass is obtained by using ceramic-plastic bonding agents or plastic-plastic bonding agents.

8. The method according to claim 1, whereby the joining of the dental arch and gingiva mass is via mechanical elements.

9. The method according to claim 8, wherein the mechanical elements include guide splints, grooves, and retention elements.

10. The method according to claim 1, wherein the method eliminates fabrication of a wax model.

11. The method according to claim 1, further comprising the step of providing a data set of an edentate jaw for providing the digital data set of the denture to be produced obtained from one of: (i) an intraoral scan, (ii) a 3D scan of a silicone impression, (iii) a combination of said 3D scan and X-ray data, or (iv) a 3D scan of a dental plaster model.

* * * * *